United States Patent
Clayton et al.

(10) Patent No.: US 9,022,914 B2
(45) Date of Patent: *May 5, 2015

(54) LASER ACCELERATOR DRIVEN PARTICLE BRACHYTHERAPY DEVICES, SYSTEMS, AND METHODS

(75) Inventors: James E. Clayton, San Jose, CA (US); Paul A. Lovoi, Saratoga, CA (US)

(73) Assignees: Varian Medical Systems Inc., Palo Alto, CA (US); The Regents of the University of California, Oakland, CA (US)

(*) Notice: Subject to any disclaimer, the term of this patent is extended or adjusted under 35 U.S.C. 154(b) by 294 days.

This patent is subject to a terminal disclaimer.

(21) Appl. No.: 13/251,014

(22) Filed: Sep. 30, 2011

(65) Prior Publication Data

US 2012/0085916 A1  Apr. 12, 2012

Related U.S. Application Data

(60) Provisional application No. 61/388,723, filed on Oct. 1, 2010.

(51) Int. Cl.
| | | |
|---|---|---|
| *A61N 5/00* | (2006.01) | |
| *G21K 1/02* | (2006.01) | |
| *H05H 15/00* | (2006.01) | |
| *A61N 5/10* | (2006.01) | |
| *G21K 1/00* | (2006.01) | |

(52) U.S. Cl.
CPC ............. *G21K 1/025* (2013.01); *H05H 15/00* (2013.01); *A61N 5/1001* (2013.01); *A61N 5/1017* (2013.01); *A61N 5/103* (2013.01); *A61N 5/1067* (2013.01); *G21K 1/00* (2013.01); *A61N 2005/1022* (2013.01); *A61N 5/1071* (2013.01); *A61N 2005/1088* (2013.01); *A61N 2005/1089* (2013.01); *A61N 2005/109* (2013.01)

(58) Field of Classification Search
CPC . A61N 5/0601; A61N 5/1002; A61N 5/1014; A61N 5/1027; A61N 5/1077
USPC ............... 600/1, 3; 250/336.1, 395, 492.3; 606/13–18
See application file for complete search history.

(56) References Cited

U.S. PATENT DOCUMENTS

| | | | |
|---|---|---|---|
| 5,012,357 | A | 4/1991 | Schoeppel et al. |
| 5,562,594 | A | 10/1996 | Weeks |
| 6,086,942 | A | 7/2000 | Carden et al. |
| 6,324,257 | B1 | 11/2001 | Halavee |
| 6,419,621 | B1 | 7/2002 | Sioshansi et al. |
| 6,780,184 | B2 | 8/2004 | Tanrisever |
| 7,233,820 | B2 | 6/2007 | Gilboa et al. |
| 7,351,193 | B2 | 4/2008 | Forman et al. |
| 7,555,330 | B2 | 6/2009 | Gilboa et al. |
| 7,564,946 | B2 | 7/2009 | Gertner |
| 7,620,147 | B2 | 11/2009 | Gertner et al. |

(Continued)

OTHER PUBLICATIONS

Non-Final Office Action issued Jun. 17, 2013, in U.S. Appl. No. 13/251,047.

(Continued)

*Primary Examiner* — Jacqueline Cheng
*Assistant Examiner* — Kaylee Wilson
(74) *Attorney, Agent, or Firm* — Miles & Stockbridge P.C.

(57) ABSTRACT

A laser accelerator driven electronic brachytherapy system, device, and method for particle based treatment of a tumor or other human diseases and conditions.

53 Claims, 5 Drawing Sheets

(56) References Cited

U.S. PATENT DOCUMENTS

| | | | |
|---|---|---|---|
| 7,680,244 B2 | 3/2010 | Gertner et al. | |
| 7,680,245 B2 | 3/2010 | Gertner | |
| 7,693,258 B2 | 4/2010 | Gertner | |
| 7,776,310 B2 | 8/2010 | Kaplan | |
| 7,922,646 B2 | 4/2011 | Russell et al. | |
| 8,264,174 B2 | 9/2012 | Liu et al. | |
| 2004/0208285 A1 | 10/2004 | Freudenberger et al. | |
| 2004/0228509 A1 | 11/2004 | Holupka et al. | |
| 2004/0242953 A1* | 12/2004 | Good | 600/7 |
| 2006/0293644 A1 | 12/2006 | Umstadter | |
| 2007/0038173 A1 | 2/2007 | Simpson | |
| 2007/0254833 A1 | 11/2007 | Hunter et al. | |
| 2008/0056960 A1 | 3/2008 | Laugharn, Jr. et al. | |
| 2009/0080594 A1 | 3/2009 | Brooks et al. | |
| 2009/0314949 A1 | 12/2009 | Plettner et al. | |
| 2010/0061518 A1 | 3/2010 | Smith | |
| 2012/0085916 A1 | 4/2012 | Clayton et al. | |
| 2012/0289859 A9 | 11/2012 | Nicoson et al. | |

OTHER PUBLICATIONS

U.S. Appl. No. 13/251,047, filed Sep. 30, 2011.
Abbondanno et al., CERN n_TOF Facility: Performance Report, European Organization for Nuclear Research, Jan. 31, 2003, CERN/INTC-O-011,INTC-2002-037, CERN-SL-2002-053 ECT, n_TOF-PUB-2010-001, Geneva, Switzerland.
Amplitude Technologies, Pro-Pulse (High Energy Nd:YAG Laser), Amplitude Technologies, www,amplitude-technologies.com, 2011.
Avanesyan et al., Generation of Color Enters by Femtosecond Laser Pulses in Wide Band Gap Materials, 2001.
Beyreuther et al., Establishment of Technical Prerequisites for Cell Irradiation Experiments with Laser-Accelerated Electrons, Med. Phys. 37(4), Apr. 2010, Am. Assoc. Phys. Med., pp. 1392-1400.
Bielajew, Alex F., The Effect of Strong Longitudinal Magnetic Fields on Dose Deposition from Electron and Photon Beams, Medical Physics 20 (1993), 1171 79.
Bruhwiler et al., Particle-in-Cell Simulations of Plasma Accelerators and Electron-neutral Collisions, The American Physical Society, Physical Review Special Topics—Accelerators and Beams, vol. 4, pp. 101302-1-101302-13.
Bruhwiler et al., Particle-in-Cell Simulations of Tunneling Ionization Effects in Plasma-Based Accelerators, Physics of Plasmas, vol. 10, No. 5, May 2003, American Institute of Physics, pp. 2022-2030.
Bullinger et al., Help for AML: Methylation Profiling Opens New Avenues, Cancer Cell Previews, Cell Press, Cancer Cell 17, Elsevier Inc., Jan. 19, 2010, pp. 1-3.
Catravas et al., Femtosecond X-rays from Thomson Scattering Using Laser Wakefield Accelerators, Measurement Science and Technology 12 (2001), Institute of Physics Publishing, pp. 1828-1834.
Catravas et al., Measurement of Electron-Beam Bunch Length and Emittance Using Shot-Noise-Driven Fluctuations in Incoherent Radiation, The American Physical Society, Physical Review Letters, vol. 82, No. 26, Jun. 28, 1999, pp. 5261-5264.
Catravas et al., Radiation Sources and Diagnostics with Ultrashort Electron Bunches, Physics of Plasmas, to appear, 2002, l'OASIS Group, Center for Beam Physics, Lawrence Berkeley National Laboratory, University of California, Berkley, CA, Nov. 2, 2001.
Ceccotti et al., Proton Acceleration with High-Intensity Ultrahigh-Contrast Laser Pulses, The American Physical Society, PRL 99, 185002, Nov. 2, 2007, pp. 185002-185002-4.
Chauvie et al., Geant4 Physics Processes for Microdosimetry Simulation: Design Foundation and Implementation of the First Set of Models, Dec. 18, 2006.
Chen et al., Acceleration of Electrons by the Interaction of a Bunched Electron Beam with a Plasma, SLAC-PUB-3487, SLAC/AP-39, Nov. 1984 (A/AP).
Chen et al., Observation of Phase-Matched Relativistic Harmonic Generation, The American Physical Society PRL, vol. 84, No. 24, Jun. 12, 2000, pp. 5528-5531.
Chernayev et al., Modulation of Absorbed Dose Distributions by Magnetic Fields, Lomonosov Moscow State University Skobeltsyn Institute of Nuclear Physics, JINR University Ctr., Dubna, 2005.

Colby, Eric R., Advanced Accelerator R&D, Outlook and Strategy, SLAC, National Accelerator Laboratory, SLAC pre-SPC Meeting, May 4, 2011.
Colby, Eric R., Laser-Driven Dielectric-Structure Accelerators, Accelerator Research Dept. B, SLAC, http://www-project.slac.stanford.edu/e163/DielectricAccelTalk.pdf, Jul. 21, 2003.
Das, Indra J., Diamond Dosimetry, Dept. of Radiation Oncology, Indiana University of School of Medicine and Midwest Proton Radiation Therapy Institute (MPRI), Indianapolis, IN, ID/SS/diamond-09, 2009.
Dewa et al., Experiments of High Energy Gain Laser Wakefield Acceleration, Elsevier Science B.V., Nuclear Instruments and Methods in Physics Research A 410 (1998), pp. 357-363.
Du, Dongsu, Diagnostics for the Texas Petawatt Laser-Plasma Accelerator, Thesis, University of Texas at Austin, Aug. 2010.
Esarey et al., Electron Injection into Plasma Wake Fields by Colliding Laser Pulses, The American Physical Society, PRL, vol. 79, No. 14, Oct. 6, 1997, pp. 2682-2685.
Esarey et al., Laser-Induced Electron Trapping in Plasma-based Accelerators, American Institute of Physics, Physics of Plasmas, vol. 6, No. 5, May 1999, pp. 2262-2268.
Esarey et al., Nonlinear Theory of Nonparaxial Laser Pulse Propagation in Plasma Channels, The American Physical Society, PRL, vol. 84, No. 14, Apr. 3, 2000, pp. 3081-3084.
Esarey et al., Nonparaxial Propagation of Ultrashort Laser Pulses in Plasma Channels, The American Physical Society, PRE vol. 59, No. 1, Jan. 1999, pp. 1082-1095.
Esarey et al., Optically Guided Laser Wakefield Acceleration, Naval Research Laboratory, Washington, DC, NRL/MR/6790-93/7320, AD-A265 441, Apr. 19, 1993.
Esarey et al., Physics of Laser-Driven Plasma-Based Electron Accelerators, The American Physical Society, Reviews of Modern Physics, vol. 81, Jul.-Sep. 2009, pp. 1229-1284.
Esarey et al., Self-Focusing and Guiding of Short Laser Pulses in Ionizng Gases and Plasmas, IEEE Journal of Quantum Electronics, VO. 33, No. 11, Nov. 1997, pp. 1879-1914.
Esarey et al., Synchrotron Radiation from Electron Beams in Plasma-Focusing Channels, The American Physical Society, PRE, vol. 65, pp. 056505-1-056505-15 , May 20, 2002.
Faure et al., A Laser-Plasma Accelerator Producing Monoenergetic Electron Beams, Nature Publishing Group, vol. 431, Sep. 30, 2004, pp. 541-544.
Faure et al., Modelling Laser-Based Table-Top THz Sources: Optical Rectification, Propagation and Electro-Optic Sampling, Kluwer Academic Publishers, Optical and Quantum Electronics 36, 2004, pp. 681-697.
Filip et al., Optical Cross-Correlator Based on Supercontinuum Generation, OSA, Optics Express, vol. 14, No. 6, Mar. 20, 2006, pp. 2512-2519.
Fourkal et al., Linear Energy Transfer of Proton Clusters, Institute of Physics and Engineering in Medicine, Physics in Medicine and Biology, 56, 2011, pp. 3123-3136.
Fubiani et al., Beat Wave Injection of Electrons into Plasma Waves Using Two Interfering Laser Pulses, The American Physical Society, PRE 70, 2004, pp. 016402-1-016402-12.
Fubiani et al., Improvement of Electron Beam Quality in Optical Injection Schemes using Negative Plasma Density Gradients, The American Physical Society, PRE 73, 2006, pp. 026402-1-026402-8.
Fubiani et al., Space Charge Modeling of Dense Electron Beams with Large Energy Spreads, The American Physical Society, Physical Review Special Topics—Accelerators and Beams 9, 2006, pp. 064402-1-064402-31.
Geddes et al., Guiding of Relativistic laser Pulses by Preformed Plasma Channels, the American Physical Society, PRL 95, 145002 (2005), week ending Sep. 30, 2005, pp. 145002-1-145002-4.
Geddes et al., High Quality Electron Beams from a Plasma Channel Guided Laser Wakefield Accelerator, Jul. 2004.
Geddes et al., High-Quality Electron Beams from a Laser Wakefield Accelerator Using Plasma-Channel Guiding, Nature Publishing Group, Letters to Nature, vol. 431, Sep. 30, 2004, pp. 538-541.
Geddes et al., Laser Guiding at Relativistic Intensities at Wakefield Particle Acceleration in Plasma Channels, Aug. 8, 2004.

(56) References Cited

OTHER PUBLICATIONS

Geddes et al., Production of High Quality Electron Bunches by Dephasing and Beam Loading in Channeled and Unchanneled Laser Plasma Accelerators, APS/123-QED, Feb. 11, 2005.
Hafizi et al., Laser-Driven Acceleration with Bessel Beams, The American Physical Society, PRE vol. 55, No. 3, Mar. 1997, pp. 3539-3545.
Halvorsen, Per H., Dosimetric Evaluation of a New Design MOSFET in vivo Dosimeter, Med. Physics, vol. 32, pp. 110-117, 2005.
Hosaka et al., Pulse Radiolysis with Supercontinuum Probe Generated by PCF, Proceedings of IPAC 10, Kyoto, Japan, MOPEA035, 08 Applications of Accelerators, Technology Transfer and Industrial Relations, U02 Materials Analysis and Modification, pp. 145-147, 2010.
Hendriks et al., Picosecond High Voltage Switching of a Pressurized Spark Gap, Eindhoven University of Technology Downloaded on May 19, 2010, UTC from IEEE Xplore, pp. 587-590.
Kalashnikov et al., High-Power Ti:Sapphire Lasers: Temporal Contrast and Spectral Narrowing, the Cambridge University Press, Laser and Particle Beams (2007), 25, pp. 219-223.
Kaplan et al., Fully Relativistic Theory of the Ponderomotive Force in an Ultraintense Standing Wave, The American Physical Society, PRL 95, week ending Jul. 29, 2005, pp. 053601-1-053601-4.
Katsouleas et al., Laser Steering of Particle Beams: Refraction and Reflection of Particle Beams, Laser-Plasma Interactions, Elsevier, Nuclear Instruments and Methods in Physics Research A 455 (2000), pp. 161-165.
Katsouleas et al., Studies of Intense Propagation in Channels for Extended Length Plasma Accelerators, IEEE, 1996, pp. 773-775.
Kraft et al., Dose-Dependent Biological Damage of Tumour Cells by Laser-Accelerated Proton Beams, IOP Institute of Physics, New Journal of Physics 12 (2010) 085003, pp. 1-12.
Lawson et al., Surface Figure and Roughness Tolerances for NIF Optics and the Interpretation of the Gradient, P-V Wavefront and RMS Specifications, Part of the SPIE Conference on Optical Manufacturing and Testing III, Denver, CO, Jul. 1999, SPIE vol. 3782, pp. 510-517.
Ledingham et al., Laser-Driven Proton Oncology—A Unique new Cancer Therapy?, The British Journal of Radiology, British Institute of Radiology (2007) 80, 855-858.
Leemans et al., Gamma-Neutron Activation Experiments Using Laser Wakefield Accelerators, American Institute of Physics, Physics of Plasma, vol. 8, No. 5, May 2001, pp. 2510-2516.
Leemans et al., GeV Electron Beams from a CM-Scale Accelerator, eScholarship, University of California, Lawrence Berkeley National Laboratory, May 4, 2006, pp. 1-12.
Leemans et al., GeV Electron Beams from a Centimetre-Scale Accelerator, Nature Publishing Group, Letters, Nature Physics, vol. 2, Oct. 2006, pp. 696-698.
Leemans et al., Laser-Driven Plasma-Based Accelerators: Wakefield Excitation, Channel Guiding, and Laser Triggered Particle Injection, American Physical Society 42, Physics of Plasmas, vol. 5, No. 5, May 1998, pp. 1615-1623.
Leemans et al., Laser Guiding for GeV Laser-Plasma Accelerators, eScholarship, University of California, Lawrence Berkeley National Laboratory, Jun. 6, 2005, pp. 17.
Leemans et al., Laser Guiding for GeV Laser-Plasma Accelerators, Phil. Trans. R. Soc. A (2006) 364, pp. 585-600.
Leemans et al., New Ultrafast X-ray Sources and Their Applicattions, Femtosecond X-ray Generation Through Relativistic Electron Beam-Laser Interaction, C.R. Acad. Sci. Paris, t. 1, Série IV, 2000, Électromagnétisme, optique/Electromagnetism, optics, pp. 279-296.
Leemans et al., Observation of THz Emission from a Laser-Plasma Accelerated Electron Bunch Crossing a Plasma-Vacuum Boundary, pp. 1-4, Apr. 14, 2003.
Leemans et al., Radiation from Laser Accelerated Electron Bunches: Coherent Terahertz and Femtosecond X-rays, pp. 1-15, Aug. 18, 2004.
Leemans et al., Recent Progress on Laser Driven Accelerators and Applications, Nuclear Engineering and Technology, vol. 37, No. 5, Oct. 2005, pp. 447-456.
Leemans et al., Terahertz Radiation from Laser Accelerated Electron Bunches, American Institute of Physics, Physics of Plasmas, vol. 11, No. 5, May 2004, pp. 2899-2906.
Limpert et al., All Fiber Chirped-Pulse Amplification System Based on Compression in Air-Guiding Photonic Bandgap Fiber, OSA, Optics Express, vol. 11, No. 24, Dec. 1, 2003, pp. 3332-3337.
Linz et al., What Will It Take for Laser Driven Proton Accelerators to Be Applied to Tumor Therapy?, The American Physical Society, Physical Review Special Topics—Accelerators and Beams, 10, 094801 (2007), pp. 094801-1-094801-8.
Ma, C-M, Laser-Driven Targetry: The Road to Clinical Applications, Dept. of Radiation Oncology for Chase Cancer Center, Philadelphia, PA 19111, USA, Jul. 2009.
Malka et al., Principles and Applications of Compact Laser-Plasma Accelerators, Nature Publishing Group, Review Article, Nature Physics, vol. 4, Jun. 2008, pp. 447-453.
Mangles et al., Monoenergetic Beams of Relativistic Electrons from Intense Laser-Plasma Interactions, Nature Publishing Group, Letters to Nature, Nature, vol. 431, Sep. 2004, pp. 535-538.
Meyer-Ter-Vehn, J., From Laser Fusion to Laser Accelerators: Basic Studies into High Power Laser Plasmas, IOP Publishing Ltd., Plasma Physics and Controlled Fusion, 51, (2009) 124001, pp. 1-13.
Michel et al., Efficient Electron Injection into Plasma Waves Using Higher-Order Laser Modes, Lawrence Berkeley National Laboratory, Berkeley, CA 94720, USA, Aug. 2, 2006, pp. 1-21.
Michel et al., Radiative Damping and Electron Beam Dynamics in Plasma-Based Accelerators, The American Physical Society, PRE 74, 026501 (2006), pp. 026501-1-026501-14.
Mordovanakis et al., Quasimonoenergetic Electron Beams with Relativistic Energies and Ultrashort Duration from Laser-Solid Interactions at 0.5 kHz, The American Physical Society, PRLA 103, 235001 (2009), week ending Dec. 4, 2009, pp. 235001-1-235001-4.
Murakami et al., Radiotherapy Using a Laser Proton Accelerator, 2008.
Nabekawa et al., All-Solid-State High-Peak-Power Ti:Sapphire Laser System above 5-kHz Repetition Rate, Applied Physics B Lasers and Optics, Appl. Phys. B 70 [Suppl.], (2000)/Digital Object Identifier (DOI), pp. S171-S179.
Nakajima, Kazuhisa, Compact X-ray Sources, Towards a Table-Top Free-Electron Laser, Nature Publishing Group, News & Views, Nature Physics, vol. 4, Feb. 2008, pp. 92-93.
Nakamura et al., GeV Electron Beams from a Centimeter-Scale Channel Guided Laser Wakefield Accelerator, American Institute of Physics, Physics of Plasmas 14, 056708 (2007), pp. 056708-1-056708-8.
Olivares et al., Determination of Electron Fluence Ratios for Various Materials in an Electron Beam, Proceedings of the 22nd Annual EMBS International Conference, Jul. 23-28, 2000, Chicago, IL, IEEE, pp. 2493-2495.
Pang et al., Subluminous Phase Velocity of a Focused Laser Beam and Vacuum Laser Acceleration, The American Physical Society, PRE 66, 066501 (2002), pp. 066501-1-066501-3.
Patel, Navroz, The Plasma Revolution, Nature Publishing Group, News Feature, Nature, vol. 449, Sep. 13, 2007, pp. 133-135.
Radiabeam Technologies, LLC, Photoinjector Gun, RadiaBeam Technologies, LLC; Santa Monica, CA, www.radiabeam.com, 2011.
Reitsma et al., Simulation of Electron Post-Acceleration in a Two-Stage laser Wakefield Accelerator, pp. 1-24, 2002.
Richter et al., A Dosimetric System for Quantitative Cell Irradiation Experiments with Laser-Accelerated Protons, Institute of Physics and Engineering in Medicine, Phys. Med. Biol. 56 (2011), pp. 1529-1543.
Rogers, D.W.O., Fluence to Dose Equivalent Conversion Factors Calculated with EGS3 for Electrons from 100 keV to 20 GeV and photons from 11 keV to 20 GeV, Health Physics vol. 46, No. 4 (Apr. 1984), pp. 891-914.
Schroeder et al., Electron-Beam Conditioning by Thomson Scattering, The American Physical Society, Physical Review Letters, vol. 93, No. 19, week ending Nov. 5, 2004, pp. 194801-1-194801-4.

(56) References Cited

OTHER PUBLICATIONS

Schroeder et al., Frequency Chirp and Pulse Shape Effects in Self-Modulated Laser Wakefield Accelerators, American Institute of Physics, Physics of Plasmas, vol. 10, No. 5, May 2003, pp. 2039-2046.
Schroeder et al., Generation of Ultrashort Electron Bunches by Colliding Laser Pulses, The American Physical Society, PRE, vol. 59, No. 5, May 1999, pp. 6037-6047.
Schroeder et al., Multimode Analysis of the Hollow Plasma Channel Wakefield Accelerator, The American Physical Society, PRL, vol. 82, No. 6, Feb. 8, 1999, pp. 1177-1180.
Schroeder et al., Raman Forward Scattering of Chirped Laser Pulses, Lawrence Berkeley National Laboratory, University of California, Berkeley, CA 94720, LBNL-50729, Dec. 5, 2002, pp. 1-32.
Schroeder et al., Statistical Properties of Radiation Power Levels from a High-Gain Free-Electron Laser at and Beyond Saturation, Elsevier Science B.V., Nuclear Instruments and Methods in Physics Research, Section A 507 (2003), pp. 110-114.
Schroeder et al., Theory of Coherent Transition Radiation Generated at a Plasma-Vacuum Interface, The American Physical Society, PRE 69, 016501 (2004), pp. 016501-1-016501-12.
Schroeder et al., Trapping, Dark Current, and Wave Breaking in Nonlinear Plasma Waves, American Institute of Physics, Physics of Plasmas 13, 033103 (2006), pp. 033103-1-033103-9.
Schroeder et al., Warm Wave Breaking of Nonlinear Plasma Waves with Arbitrary Phase Velocities, The American Physical Society, PRE 72, 055401(R) (2005), pp. 055401-1-055401-4.
Shadwick et al., Fluid and Vlasov Models of Low-Temperature, Collisionless, Relativistic Laser-Plasma Interactions, Jan. 16, 2005, pp. 1-24.
Shadwick et al., Hamiltonian Description of Low-Temperature Relativistic Plasmas, The American Physical Society, PRL, vol. 93, No. 17, week ending Oct. 22, 2004, pp. 175002-1-175002-.
Sprangle et al., Propagation of Intense, Short Laser Pulses in the Atmosphere, Naval Research Laboratory, Washington, DC 20375-5320, NRL/MR/6790-02-8603, Apr. 10, 2002, pp. 1-26.
Suk et al., Plasma Electron Trapping and Acceleration in a Plasma Wake Field Using a Density Transition, The American Physical Society, PRL, vol. 86, No. 6, Feb. 5, 2001, pp. 1011-1014.
Teunissen, Hein, Multipass Amplifier for Terawatt Ti:Sapphire Laser System, Theory, Construction and Characterization, University of Twente, Laser Physics and Nonlinear Optics, Dept. of Science & Technology, Enchede, Oct. 12, 2007, pp. 1-69.
Ting et al., Effects of Radiation Damping on Beam Quality in the Inverse Free-Electron Laser Accelerator, Gordon and Breach Science Publishers, Inc., Particle Accelerators, 1987, vol. 22, pp. 149-160.
Ting et al., Plasma Wakefield Generation and Electron Acceleration in a Self-Modulated Laser Wakefield Accelerator Experiment, American Institute of Physics, Physics Plasmas 4 (5), May 1997, pp. 1889-1899.

Tóth et al., Tuning of Laser Pulse Shapes in Grating-Based Compressors for Optimal Electron Acceleration in Plasmas, Optical Society of America, Optics Letters, vol. 28, No. 19, Oct. 1, 2003, pp. 1823-1825.
Travish, Gil, Light Sources Based on Optical-Scale Accelerators, Particle Beam Physics laboratory, UCLA Department of Physics & Astronomy, UCLA, 2010.
Travish, Gil, The Micro Accelerator Platform: A Potential Injector for a DLA Based Collider, Particle Beam Physics laboratory, UCLA Department of Physics & Astronomy, UCLA, 2009.
Trines et al., On the Effect of Laser and Plasma parameters on Stimulated Raman Scattering and Fast-Electron Generation, Cambridge University Press, J. Plasma Physics (2005), vol. 71, Part 4, pp. 411-433.
Uesaka et al., Generation of Femtosecond Electron Single Pulse Using laser Photocathode RF Gun, 1998.
Umstadter et al., Developments in Relativistic Nonlinear Optics, American Institute of Physics, Superstrong Fields in Plasmas, 2002, Second Int'l Conf., pp. 95-103.
Van Tilborg et al., Pulse Shape and Spectrum of Coherent Diffraction-Limited Transition Radiation from Electron Beams, eScholarship, University of California, Lawrence Berkeley National Laboratory, Dec. 20, 2003, pp. 1-23.
Van Tilborg et al., Temporal Characterization of Femtosecond Laser-Plasma-Accelerated Electron Bunches Using Terahertz Radiation, The American Physical Society, PRL 96, 014801 (2006), week ending Jan. 13, 2006, pp. 014801-1-014801-4.
Van Tilborg et al., THz Radiation as a Bunch Diagnostic for Laser-Wakefield-Accelerated Electron Bunches, eScholarship, University of California, Lawrence Berkeley National Laboratory, Feb. 15, 2006, pp. 1-30.
Volfbeyn et al., Guiding of Laser Pulses in Plasma Channels Created by the Ignitor-Heater Technique, American Physical Society, Physics of Plasmas, vol. 6, No. 5, May 1999, pp. 2269-2277.
Walker et al., Ups and Downs of Nuclear Isomers, American Institute of Physics, Physics Today, Jun. 2005, pp. 39-44.
Wang et al., Vacuum electron Acceleration by an Intense Laser, American Institute of Physics, Applied Physics Letters, vol. 78, No. 15, Apr. 9, 2001, pp. 2253-2255.
Wille et al., Teramobile: A Mobile Femtosecond-Terawatt Laser and Detection System, The European Physical Journal Applied Physics, Eur. Phys. J. AP 20, (2002) pp. 183-190.
Yoder et al., Laser-Powered Dielectric Structure as a Micron-Scale Electron Source, Proceedings of PAC07, Albuquerque, New Mexico, USA, THPMS071, 03 Linear Colliders, Lepton Accelerators and New Acceleration Techniques, A14 Advanced Concepts, pp. 3145-3147, 2007.
Zhang et al., Microwave Inverse Free-Electron-Laser Accelerator Using a Small "Phase Window", The American Physical Society, PRE, vol. 50, No. 2, Aug. 1994, pp. 1491-1495.

\* cited by examiner

MCNPX Problem Geometry 3 cm Water 3 cm Tumor
10 Shells

Problem cut off

Air

Zoom in of Geometry

Stippling is Water

White is Void

Source

10 MeV Electrons incident on a 3 cm Sphere of water

10 cm Sphere of air 6 cm Sphere of water 3 cm Sphere of water

1000 KeV-10 MeV Electrons incident normally directed at the tumor R=3.05 cm

10 MeV Electrons incident on a 3 cm Sphere of Water

10 - 0.3 cm Spherical Shells

Tracks for 10 incident electrons

Dose Distribution for 10 MeV electrons incident on a 3 cm radius Water Sphere

Data from MCNPX Simulation 10 MeV Electrons on 3 cm Water Sphere

| Radius | Gy in 5 min | Error |
|---|---|---|
| 0.3 | 60.16 | 0.29 |
| 0.6 | 59.93 | 0.23 |
| 0.9 | 59.99 | 0.19 |
| 1.2 | 59.78 | 0.15 |
| 1.5 | 59.10 | 0.12 |
| 1.8 | 57.90 | 0.10 |
| 2.1 | 56.36 | 0.09 |
| 2.4 | 54.77 | 0.08 |
| 2.7 | 53.31 | 0.07 |
| 3 | 52.55 | 0.05 |
| 6 | 3.07 | 0.00 |
| Ratio of Center/Outer 3 cm | 19.6 | |

Average Dose = 57.4 Gy
Standard Deviation = 2.9 Gy

Assumptions
100 Hz Laser Rep Rate

LASER ACCELERATOR DRIVEN PARTICLE BRACHYTHERAPY DEVICES, SYSTEMS, AND METHODS

CROSS-REFERENCE TO RELATED APPLICATIONS

This application claims priority to and the benefit of U.S. Provisional Application No. 61/388,723, filed on Oct. 1, 2010, the content of which is incorporated herein by reference in its entirety.

FIELD

The present disclosure relates generally to a system, apparatus, and method for administering radiation internal or adjacent to a patient, and more particularly to a particle-based electronic brachytherapy system, method, and computer program product for administering a treatment dose to a patient.

BACKGROUND

Brachytherapy is a form of radiotherapy (radiation therapy) used for the treatment of conditions (tumors, for example) of the mammalian body with radiation from within the body rather than external to the body. Because brachytherapy is localized and precise, it is commonly used as an effective radiation treatment for various forms of cancers, such as, but not limited to, cervical, prostate, breast, lung, esophageal, head and neck, and skin cancers. Brachytherapy is typically divided into Low Dose Rate (LDR) brachytherapy and High Dose Rate (HDR) brachytherapy. LDR typically has a dose rate of 40 to 60 cGy/hour (centi-Gray per hour) whereas HDR typically has a dose rate of hundreds (100's) of cGy/minute.

Generally, in HDR brachytherapy systems, one or more thin catheters are first placed in or near the condition within the body and then highly radioactive pellets containing man-made or natural radioactive isotopes are delivered (pushed) into each of the guide catheters. The radioactive sources or seeds are placed in or near the condition, and a high radiation dose (i.e., ionizing radiation, usually X-rays and gamma rays or beta particles from the decay of the isotope) is administered directly to the tumor or tumor bed after a tumor is excised while reducing the radiation exposure in the surrounding healthy tissues and organs. A treatment planning system (TPS) is generally used to determine the optimized treatment for a given condition. This treatment plan is produced to meet the treatment prescribed by the physician. The treatment plan is transferred to or is part of a controller that controls how long the source stays in each dwell position. Each of the plurality of guide catheters may have a number of dwell positions. After a series of treatments, the guide catheters are removed, and there are no radioactive seeds left in the body. Isotope-based brachytherapy systems, however, cannot be turned on and off at will.

Brachytherapy has numerous advantages over other therapies, such as External Beam Radiation Therapy (EBRT), Intensity Modulated Radiation Therapy (IMRT), and Imaged Guided Radiation Therapy (IGRT). For example, in contrast to EBRT, IMRT, and IGRT where high energy X-rays (photons) or electrons are directed at a condition within the body from outside of the body, brachytherapy can treat the condition within the body without delivering radiation through a larger volume of healthy tissue. In contrast to IGRT, in situations where the patient moves or the location of the condition to be treated moves during the treatment (e.g., lung, breast or prostate tumor moving during breathing), the radiation source in brachytherapy retains its correct position in relation to the condition during the treatment, whereas the radiation needs to be guided based on images of the patient or surrogates attached to the patient in IGRT.

EBRT, IMRT and IGRT treatment systems and devices, however, have an advantage over conventional isotope-based brachytherapy systems and devices in that they can be turned on and off at will and there is no residual radioactivity when they are turned off.

Electronic brachytherapy (EBT) is a form of brachytherapy that uses micro miniature accelerators as the radiation source rather than natural or man-made radioisotopes to produce X-rays (photons). Thus, electronic brachytherapy (EBT) has all the advantages of EBRT, IMRT and IGRT, since it can be turned on and off at will, and does not contain any radioactive isotopes. Additionally, just as the isotope-based brachytherapy source, it is contained within the body near or within the condition being treated. Several companies (Xoft, Inc., AXXENT and Carl Zeiss INTRABEAM, for example) have developed EBT systems based on high voltage single stage DC accelerators. The radiation source in these systems is a miniature 50 $kV_p$ X-ray source producing low energy X-rays (photons).

Electronic brachytherapy, just like other photon (or X-ray) based therapy treatments, are especially suited for treating cervical, prostate, breast, and lung cancers. Many medical devices have been developed for cervical cancer brachytherapy. An early device was the Fletcher-Suit cervical applicator. The Fletcher applicator provided a method for intracervical or intrauterine guiding of radioactive sources. Derivatives of this device have been developed, for example in Weeks, U.S. Pat. No. 5,562,594; a modified Fletcher tandem device provides shielding for healthy tissue such as the adjacent rectum. Weeks contains a comprehensive dissertation of the physics and anatomy of intracervical brachytherapy, it is incorporated herein by reference. Schoppel et al., U.S. Pat. No. 5,012,357, describes an intracavity brachytherapy applicator that allows inserting and removing shielding for protecting critical structure but allowing computer tomography (CT) imaging without artifacts. Cervical cancer is well treated with radiation but the collateral damage is still of concern. A great deal of effort has gone into shielding critical structures from excess radiation. The need for improved treatment still exists, especially because over 12,000 new cases of cervical cancer are expected to be diagnosed in the US each year with nearly 4,000 deaths.

There are approximately 190,000 new diagnosis of prostate cancer in the US annually with over 32,000 deaths, a significantly lower death rate than cervical cancer. Prostate cancer is well treated with a variety of hormone suppression, radiation and surgical techniques. Low Dose Radiation (LDR) brachytherapy using seed placement was the predominant new treatment over the last decade but advances in IMRT have begun to replace or supplement seeds. Unfortunately, regardless of which approach is used, the effect on quality of life due to collateral damage is still significant.

Lung cancer is the leading cause of cancer deaths in the United States and it claims more lives than colon, prostate and breast cancer combined. Over 196,000 patients are diagnosed with lung cancer each year in the United States and nearly 160,000 die of it. Lung cancer patients are poorly serviced by the current treatment protocols. Cancer tumors in the lung are constantly moving when the patient breathes making precise targeting for IGRT difficult. A new treatment for treating lung cancer is still needed.

In each of the above-described examples, electronic brachytherapy (EBT) provides an advantage. However, photon-based electronic brachytherapy still delivers a significant radiation dose to healthy tissue, which can have serious medical consequences. Moreover, for larger tumors where megavolt (MeV) level treatment is necessary, or where the exponential isotope decay does not produce the desired radiation dose profile, particles, such as electrons, protons, neutrons and heavy ions might be more suitable instead of photons for the treatment.

Current electronic brachytherapy devices, however, do not use particles, such as electrons, protons, neutrons and heavy ions, as the radiation beam source. Instead, X-ray photons are used as the radiation source. Even though, high voltage gradients are used to accelerate particles, typically electrons, these electrons are converted to photons through the Bremsstrahlung radiation process (electrons striking a target) and the photons are used as the treatment radiation, because the electrons are too low in voltage and cannot be used directly in therapy. The Continuously Slowing Down Approximation range of a 50 keV electron is 0.0433 mm (NIST. ESTAR Program). Also, the acceleration potential that is achieved using the currently available high voltage gradients is limited to about 10 MeV/m, which limits the particle voltage to about 100 keV or less in a typical electronic brachytherapy device suitable to be inserted into the body (about 10 mm in length).

In order to use particles such as electrons, protons and heavy ions for brachytherapy treatment, the energy of the particles need to be in the range of at least 5 to 70 MeV. The currently available high voltage gradients are therefore, not suitable for high energy particle generation. The current state of the art superconducting RF cavities produce about 40 MeV/m on a production basis.

SUMMARY

Particle-based electronic brachytherapy systems, devices, methods, and computer program products for treatment of conditions within the body of a patient are disclosed. The electronic brachytherapy devices can emit particles having energies in the 5-70 MeV range to be used directly for therapeutic treatment of tumors or any other human conditions and diseases. The emitted particles can include electrons having energies in the range of 5-30 MeV, protons having energies in the range of 5-70 MeV, and heavy ions having energies of at least 70 MeV/nucleon. Particle-based brachytherapy is especially advantageous where critical structures need to be protected or in areas of the body where there can be undesirable complications from exposing healthy tissue to radiation, for example, spinal cord, optic nerves, liver, brain and/or lung.

In an embodiment, a particle-based electronic brachytherapy device can include an applicator (catheter) and a high energy particle source, such as, but not limited to, a laser plasma accelerator. The laser plasma accelerator can be a compact, miniature laser-based plasma accelerator with a voltage gradient suitable to generate particles having energies in the range of 5-70 MeV. Electrons, protons, and heavy ions with acceleration gradients of 30 GeV/m to 200 GeV/m can be obtained with the compact, miniature laser plasma accelerator.

In another embodiment, a particle-based electronic brachytherapy device can include and applicator (catheter) and a high energy particle source, such as, but not limited to, a laser driven dielectric accelerator. The laser driven dielectric accelerator can be a compact, miniature dielectric accelerator with a voltage gradient suitable to generate particles having energies in the MeV range. The laser driven dielectric accelerator can include a laser driven dielectric accelerator structure as described in "Laser-Driven Dielectric-Structure Accelerators" by Eric R. Colby, "Light sources based on optical-scale accelerators" by Gil Travish, and "The Micro Accelerator Platform: A Potential Injector for a DLA Based Collider" by Gil Travish, all incorporated herein by reference in their entirety.

Accelerated electron beams achieved using any of the above described laser driven accelerators can be further used to generate secondary radiation sources. The secondary radiation sources can include X-rays, gamma rays, neutrons, and any other particles. Accelerated proton beams can also be used to generate secondary radiation sources, such as neutrons or alpha particles.

In another embodiment, a laser plasma accelerator positioned within the applicator and having a voltage gradient between 30 GeV/m and 200 GeV/m to drive electrons in a plasma via Wakefield acceleration is disclosed. The laser plasma accelerator includes an accelerator channel having a diameter between 50-400 micrometers and a length in a range of 1-2 mm, the accelerator channel including a low density gas therein which is ionized upon exposure to a laser pre-pulse or to an electrical discharge. A laser focusing device focuses a Wakefield laser pulse into the accelerator channel to push electrons in the plasma off of their nucleus, the electrons being accelerated while riding the wake of the Wakefield laser pulse to a voltage in the range of 5-70 MeV. The laser pre-pulse is either a leading edge of the Wakefield laser pulse or a separate laser pulse provided by a laser source which can be a different laser source from the laser source providing the Wakefield laser pulse. In an alternate embodiment, the accelerator channel can have a diameter between 100-250 micrometers.

A particle-based electronic brachytherapy system is disclosed including a brachytherapy device as described in any one of the embodiments above. The system also includes one or more radiation dosimeters to detect and verify actual doses delivered to one or more locations near the tissue to be irradiated. The feedback from the dosimeters can be used to change a predetermined treatment plan in real time or near real time (within a fraction of the real time).

A treatment planning software stored in a non-transitory computer readable medium is also disclosed to model particle (electron, proton, etc.) therapy when the particle source is inside the body of a patient. The treatment planning software can include treatment prescriptions, dwell positions, and/or the particle type as inputs, and particle energy, and/or dwell time as outputs. The treatment planning software, when executed, allows a source applicator (catheter) to move with a portion of an organ containing a condition to be treated (tumor, for example), keeping the tumor and treatment source aligned at all times.

Also, a sequence of programmed instructions is disclosed embodied upon a computer-readable storage medium for treating a condition within the body of a patient based on particle brachytherapy so that when a computer processing system executes the sequence of programmed instructions embodied on the computer-readable storage medium it causes the computer processing system to perform the steps of: generating a treatment plan based on treatment prescription, particle type, and particle dwell time, delivering particle radiation treatment based on the treatment plan, acquiring particle radiation information from one or more radiation sensors, determining particle energy and particle dwell time based on the acquired information, outputting the particle information, and adjusting the treatment plan based on the outputted information.

BRIEF DESCRIPTION OF THE DRAWINGS

The drawings described herein are for illustration purposes only and are not intended to limit the scope of the present disclosure in any way. The invention will be best understood by reading the ensuing specification in conjunction with the drawing figures, in which like elements are designated by like reference numerals. As used herein, various embodiments can mean some or all embodiments.

DETAILED DESCRIPTION

Electronic brachytherapy devices, systems, and methods providing particles, such as electrons, protons, neutrons, and heavy ions, for therapeutic treatment of tumors or any other human conditions and diseases are disclosed.

Figure 1:
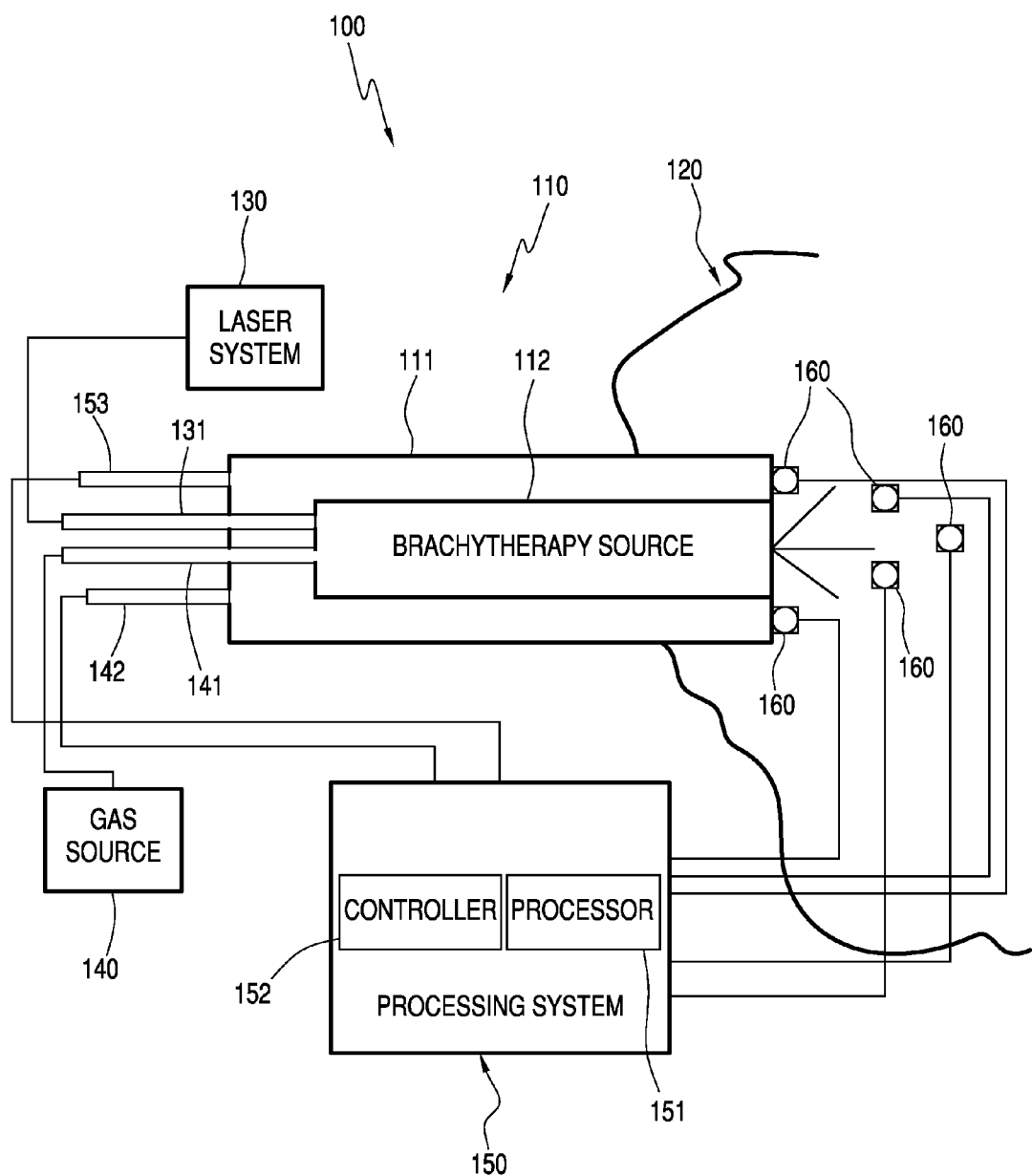
FIG. 1 is a schematic view of a particle-based electronic brachytherapy system, in accordance with an embodiment of the invention.

FIG. 1 shows a laser based accelerator driven electronic brachytherapy system 100 configured to deliver therapeutic doses of electrons, protons, neutrons, or heavy ions, directly to a region of interest, such as a tumor, tissue, or other structure, located within the body 120 of a patient within a relatively short period of time (few minutes).

The brachytherapy device 110 includes a brachytherapy source 112 and a brachytherapy applicator (catheter) 111. The applicator 111 including the source 112 can have, for example, a diameter of between 0.5-6 mm, and a length between 2-10 mm. The brachytherapy device 110 is configured to emit particles, including, but not limited to, electrons, protons, neutrons and heavy ions, having energies in the range of 5-70 MeV (at least 70 MeV/nucleon for ions) for direct treatment of the condition, such as but not limited to, a tumor within the body of a patient.

The brachytherapy device 110 mimics the penetration and dose rate of certain natural or man-made isotopes but does so without using radioactive materials and without using micro miniature X-ray tubes typically used as the photon source in an electronic brachytherapy device. Instead, the brachytherapy device 110 uses laser driven accelerators as the basis for a source of high energy particles, such as, but not limited to electrons, protons, heavy ions, etc.

In an embodiment where a laser driven plasma accelerator is the particle source, the laser driven brachytherapy device 110 uses plasma waves as the source of the high energy particles. The plasma wave is an attractive acceleration medium because particles, such as electrons, for example, can be accelerated to energies in the range of about 5-30 MeV, and electrons in this energy range can be directly used to treat the tumor or any other condition within the body. Laser particle acceleration uses high peak power laser systems to drive electrons in the plasma and accelerate them to very high energies. To accelerate the particles to the required energies, a technique called plasma Wakefield acceleration can be used. This technique uses an electric field associated with an electron plasma wave driven by an intense laser pulse. The wave can be created through the passage of a brief laser pulse into plasma within the accelerator cavity (chamber). As the pulse travels through the plasma, the electric field of the pulse separates the electrons and nucleons. Since the electrons are much lighter than the nucleons they move much further during a very short period of time, leading to a charge separation. As the laser pulse leaves the vicinity, the electrons are pulled back toward the center by the remaining positive charge of the ions that did not move. As they fall into this positive area they pick up speed, so that when they reach the center they pile up briefly before losing this energy in collision and eventually flattening out into a more even distribution. Although the electrons are not moving very quickly during this period, microscopically it appears that a bubble of charge is moving through the plasma at close to the speed of light (bubble is the region cleared of electrons followed by the region where the electrons fall back into the center). The bubble is negatively charged. This leads to a small area of a very strong potential gradient following the laser pulse. This Wakefield is used for particle acceleration. Thus, when a particle, such as, an electron is injected into the plasma near the high-density area, it will accelerate toward or away from it. This acceleration continues until the electron eventually reaches the speed of the Wakefield.

To produce a Laser Wakefield Accelerator (LWA), a low density gas, such as, but not limited to, hydrogen, is ionized by either an electrical discharge through the gas or by a laser pre-pulse provided by a second laser or as the leading edge of the Wakefield laser pulse. The Wakefield laser pulse is focused into an accelerator cavity (channel, chamber). The momentum of the light in the laser pulse separates the electrons from the positive ions. The separated electrons ride the wake of the laser pulse and are rapidly accelerated to high voltage. The ions that are left behind can also be accelerated by following the electrons. The laser plasma accelerator can have a voltage gradient between 30 GeV/m and 200 GeV/m to drive the electrons in the plasma via Wakefield acceleration. The laser plasma accelerator can include an accelerator channel having a diameter between 50-400 micrometers, and more preferably between 100-250 micrometers, and a length between 1-2 mm. A laser focusing device can be used to focus the Wakefield laser pulse into the accelerator channel to push electrons in the plasma off of their nucleus, the electrons being accelerated while riding the wake of the Wakefield laser pulse to a voltage in the range of 5-70 MeV. The laser pre-pulse is either a leading edge of the Wakefield laser pulse or a separate laser pulse provided by a separate laser source.

Figure 2A:
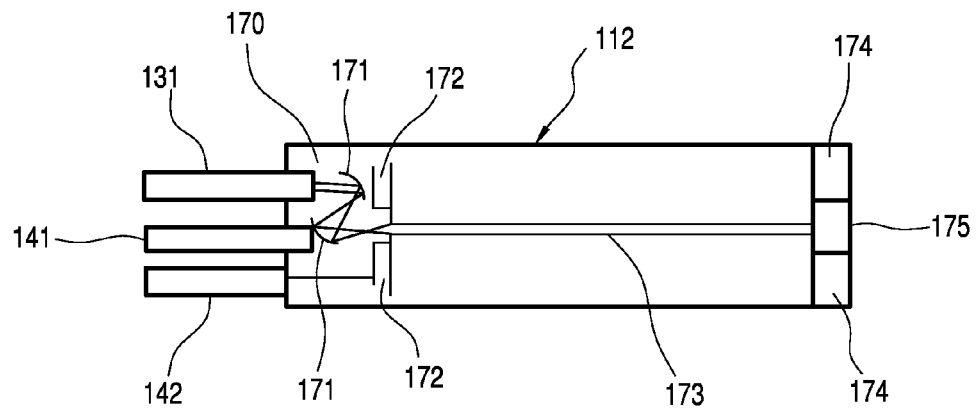
FIG. 2A is a schematic view of a laser plasma accelerator as a brachytherapy source, in accordance with an embodiment of the invention.

FIG. 2A shows a compact miniature laser plasma accelerator (LPA) which can be used as a brachytherapy source 112 to generate particles having energies in the range of 5-70 MeV. The laser plasma accelerator (LPA) 112 includes an accelerator cavity 170 with a plasma region, high voltage electrodes 172 to generate and properly prepare the plasma, high voltage delivery cables 142 to deliver the necessary high voltage to the high voltage electrodes 172, focusing optical elements 171 (mirrors, or lenses, for example) for focusing the incoming laser pulse onto a plasma generating target, a laser pulse delivery system 131 (optical fibers, for example) for delivering the laser beam into the accelerator cavity 170 and onto the focusing optical elements 171, a guide channel 173 to guide the laser pulse along a lengthwise direction of the accelerator cavity 170, ground electrodes 174, and a laser beam dump (not shown) to dispose of the laser beam after the particles are accelerated to the desired energy level.

The compact miniature laser plasma accelerator 112 uses laser driven plasma waves as the basis for a source of high energy particles. The compact miniature laser plasma accelerator 112 can use Laser Wakefield Acceleration (LWA) to accelerate the particles to energies of 5-70 MeV in a distance less than a few millimeters, thereby generating particle beams to be used directly to treat a condition within the body 120 of the patient. The working chamber (accelerator channel or cavity) of the Laser Wakefield Accelerator (LWA) can be between 50-400 micrometers, and more preferably, between 100-250 micrometers, in diameter and about 1-2 mm in length. Since the working chamber of the LWA is about 50-400 micrometers in diameter and is about 1-2 mm long, and since the acceleration length in the LWA with an acceleration gradient of 30 GeV/m needed to generate a 30 MeV treatment voltage is about 1 mm, a Laser Wakefield Accelerator based electronic brachytherapy source 112 generating an acceleration gradient of 30 GeV/m to 200 GeV/m can be built within the size of current isotope brachytherapy sources, which is about 0.8 mm in diameter and about 3 mm long.

A remote laser system 130, which is a chirped pulse amplification system (CPA), for example, can be used to generate the pulse or pulses of laser light. Chirped pulse amplification (CPA) is a technique for amplifying an ultra-short laser pulse, with the laser pulse being stretched out temporally and spectrally prior to amplification. The beam of laser light generated from the laser system 130 can be delivered and directed into the accelerator cavity 170 using a fiber optics delivery system 131. The fiber optic delivery system 131 can include hollow fibers to allow delivery of high peak power laser pulses without destroying the surfaces of the fibers. The hollow fibers can deliver amplified but not compressed laser pulses from the chirped pulse amplification system to the laser plasma accelerator. The fibers in the fiber optic delivery system can also contribute to the final compression of the laser pulse.

A rigid hollow tube can also deliver the high peak power laser pulse to the laser plasma accelerator 112. The rigid hollow tube can have a diameter of 1 to 6 mm, and a length of 25 to 400 mm. The rigid hollow tube can be evacuated, or filled with a gas that compresses the pulse width of the high peak power laser pulse.

The beam of laser light delivered and directed into the accelerator cavity 170 using the fiber optics delivery system 131 is next focused through a set of focusing optical elements 171, such as, but not limited to, optical mirrors or lenses 171, onto the plasma generating target. The target is any material, but is preferably gas which can be supplied into the plasma region as a jet of gas from an external gas source 140 through a gas delivery device 141. Any suitable gas may be used, including, but not limited to, hydrogen, helium, etc., for example. Electrons are injected into the Wakefield either using a single laser pulse to drive the Wakefield to large enough amplitudes, or several laser pulses, a first pre-pulse to create a Wakefield and a second injection pulse to inject the electrons into the Wakefield. When several laser pulses are used, the laser pulses collide in the plasma and their interferences creates an electromagnetic pattern that pre-accelerates some of the electrons. A fraction of these electrons have enough energy to be trapped in the Wakefield and driven by the pump pulse can be further accelerated. When several laser pulses are used, the first pre-pulse is delivered into the accelerator cavity 170 using an optical fiber which is separate from the optical fiber used for the second laser pulse. In an alternative embodiment, the pre-pulse laser pulse can be delivered into the accelerator cavity 170 through the same optical fiber as the second laser pulse. In either method, however, the electrons injected into the Wakefield have sufficient initial energies so that they can be trapped and accelerated and so that the laser plasma accelerator 112 receives the high power laser input necessary to operate correctly. To save laser energy and extend the acceleration length, the guiding channel 173 included into the acceleration cavity 170 guides the laser beam over a longer distance. The accelerated electrons exit the laser plasma accelerator 112 through an exit port 175, which is an output foil, for example.

To operate properly, the laser plasma accelerator 112 requires a very high peak power laser input. To achieve the necessary high peak power input in the laser plasma accelerator 112, a laser oscillator output of the chirped laser amplification system (CPA) 130 is amplified by one or more stages of amplifiers to achieve the energy per pulse required. Laser amplifiers require the beam to traverse through the gain medium which is typically a glass or crystal material. Because of the very short pulses used, damage to the amplifier can occur, due to high peak power, as the beam energy is amplified. To avoid this problem the oscillator output is temporally stretched using spectral dispersion. The resulting longer pulse is safely amplified to the necessary energy levels but with a lower peak power density due to the longer pulse duration. The pulse then needs to be temporally compressed to raise the peak power to the levels necessary for the laser plasma accelerator (LPA) 112. The compression of the pulse is done with reflective optics again using spectral dispersion as in the initial pulse stretching. The refractive optical system is aligned so that one side of the grating is further away from the approaching beam and the other end of the grating is closer. To deliver the laser pulse in a flexible way to the accelerator cavity 170, a flexible optical fiber 131 may be used. However, high peak power density may damage the fibers, especially the entrance and exit interfaces. To eliminate or reduce the damage to the optical fibers 131, hollow fibers may be used to deliver the amplified but not compressed laser pulse from the chirped laser amplification system (CPA) 130 to the accelerator cavity 170 of the laser plasma accelerator (LPA) 112. This would also effectively provide temporal compression of the pulse. The rigid hollow tubes can have lengths of 25 to 400 mm, and diameters of 1 to 6 mm. The rigid hollow tubes can also be evacuated or filled with a gas that compresses the pulse width of the high peak power laser pulse.

Additionally, the final chirped process can be carried out with a "staged by length" fiber optic array. Since the speed of different wavelengths light is different in a given medium the power can be split into several frequencies then by staging various lengths of material, the time can be adjusted such that all wavelengths arrive at the same time and at the right location such that they all coherent and so that the power is very high for a short time. This could mean 0.5-20 TW/cm$^2$ for times ranging from 50-1000 fs (1 TW=TeraWatt=$10^{12}$ W and 1 fs=femtoseconds=$10^{-15}$ s). A CPA system, as discussed above, takes a short pulse from a laser oscillator and uses spectral dispersion to lengthen the pulse to where it can safely be amplified. The spectral dispersion can then be used to remove the chirp and compress the amplified pulse. The amplified laser pulse can be delivered to the accelerator 112 by means of the fiber optics 131. The laser pulse peak power stays within the laser induced damage threshold of the material through which it must pass. To provide both, the transmission of the laser pulse through a fiber 131 to the accelerator 112, and compressing the laser pulse, a series of fibers may be used in conjunction with a dispersive element. A dispersive element, such as an optical grating, can be used to send different wavelengths of light into different paths. The light from each path can be injected into a series of fibers that have lengths designed to deliver the light from the dispersive element, which have taken different path lengths and deliver them to the accelerator at the same time. Each fiber has the correct length, depending on the wavelength of the light it collects and the dispersion of the dispersive element.

Electrons are efficient at delivering dose to a tumor location than are X-rays. For example, the dose factor for electrons having energies of about 10 MeV is $6.7*10^{-5}$ Gy/h (electrons/$cm^2$-s)$^{-1}$, while for a 10 MeV photon the factor is $9.76*10^{-8}$ Gy/h (photons/$cm^2$-s)$^{-1}$. Thus, the ratio of electron dose to photon dose is ~686:1, which means that it takes a much weaker fluence of electrons to deliver a given dose. Also, electrons have a much more precise range in tissue or water when compared to photons. Therefore, energetic electrons are better suited for delivering a more focused high dose of radiation to treat a condition, such as a tumor, within the body 120 of a patient. For protons the situation is even more precise. This is due to the energy loss mechanism of the heavier charged particle. Protons and ions have a Bragg Peak which has most of the energy transfer to the tumor site occurring at the end of the proton or ion range. Moreover, the beam energy and the beam power can be adjusted based on the particular application. For example, the particle beam energy can be adjusted based on the size or the type of the tumor to be treated. Adjusting the range according to the particular application allows for better dose distribution in tumors that are hypoxic or have an oxygen enhancement ratio.

Heavy ions and protons can also be accelerated in the laser plasma accelerator (LPA) 112. Laser pulse duration, energy, and frequency, as well as the target type and contaminants present at the target surface, and whether or not the plasma electrons are heated, are variables that can determine and control the generation of accelerated ions and protons. The laser plasma accelerator (LPA) 112 can generate accelerated protons having energies in the range of 5-70 MeV. Protons and heavy ions have the distinct advantage that they deposit the majority of their energy at the end of the range (Bragg Peak). This can lead to improved dose distributions that in principle can be even more uniform than those of electrons. This is a significant improvement over any external beam therapy approach. Moreover, currently available proton or carbon ion accelerators are large facilities that can weigh over 100 tons and have 10-15 meters in diameter. Obviously, currently available systems are not suitable to be used as ion beam sources inserted into a patient.

The laser plasma accelerator (LPA) 112 can also be used for generating neutrons from nuclear reactions induced by the accelerated protons or electrons. This could potentially lead to enhancements in the field of Boron Neutron Capture Therapy (BNCT). Additionally, the laser plasma accelerator (LPA) 112 can also be used for generating ultra short, high quality X-rays. The X-rays can be generated using the accelerated electrons already obtained through the laser plasma Wakefield acceleration process. Alternatively, the laser plasma accelerated electrons can be directed/injected into a solid target, such as, but not limited to, a high atomic number material, such as, Tungsten or Tantalum, for example, positioned at the end of the laser plasma accelerator 112. Allowing the exiting, through aperture 175, electrons to strike the target can create X-rays via the Bremsstrahlung process (Bremsstrahlung occurs when the electron strikes a target and the electric field of the target nucleus slows down the incident electron). The energy of the emitted X-rays can be adjusted by adjusting the electron energy. The generated X-rays can be used for treatment and/or for imaging. Additionally, because the accelerated electron beam energy is high, gamma rays and even neutrons or other particles can be generated as secondary radiation sources.

Figure 2B:
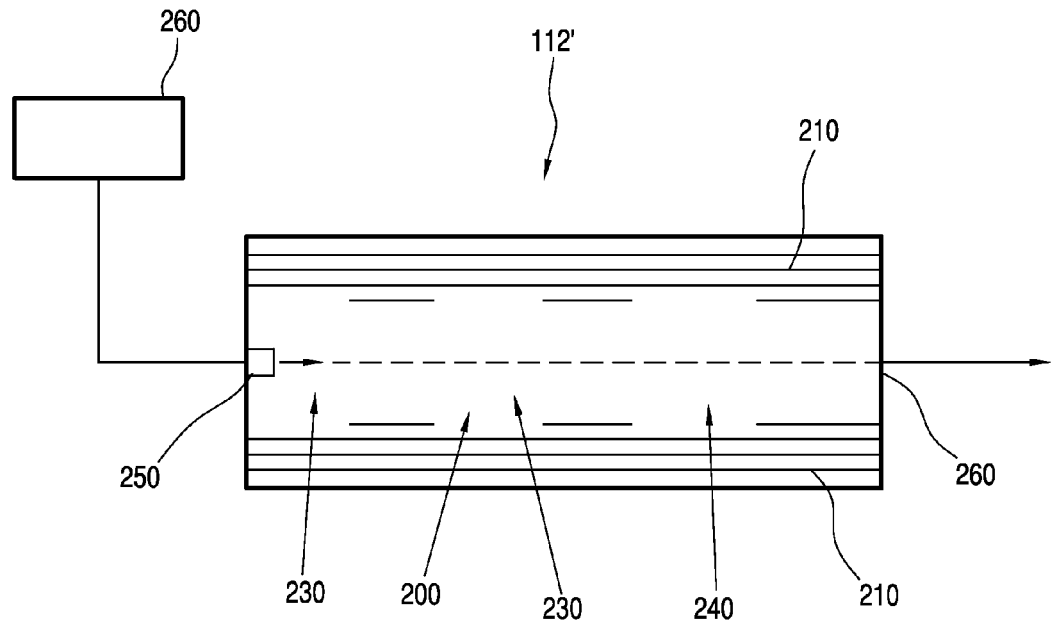
FIG. 2B is a schematic view of a laser driven dielectric accelerator as a brachytherapy source, in accordance with an embodiment of the invention.
Figure 3:
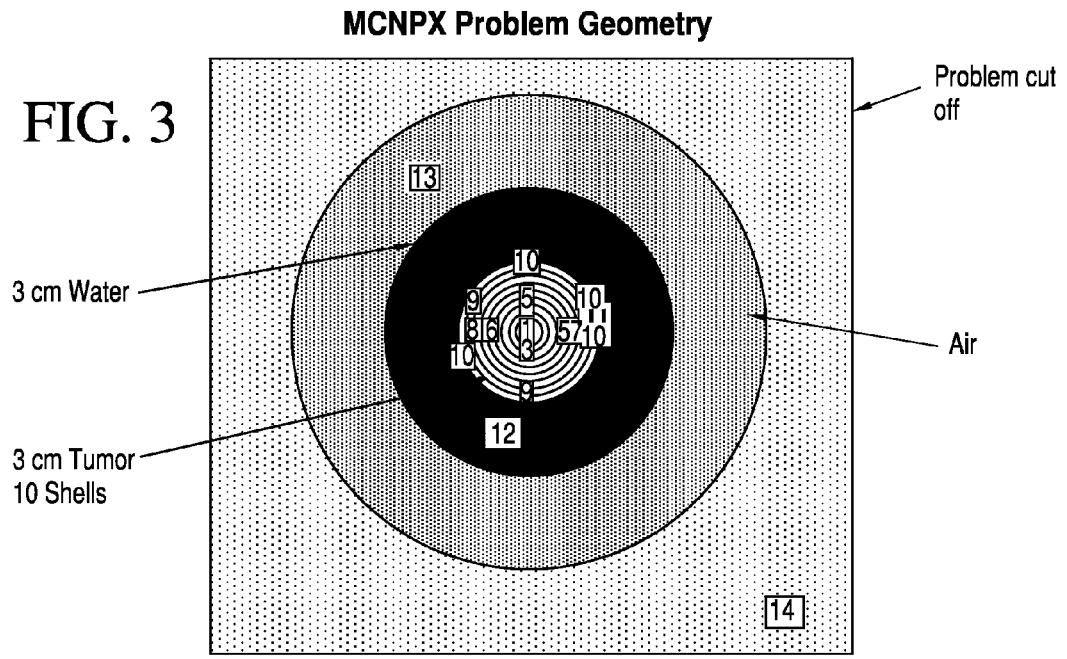
FIGS. 3-6 are different views showing simulation results for 10 MeV electrons incident on a 3 cm sphere of water, in accordance with various embodiments of the invention.
Figure 4:
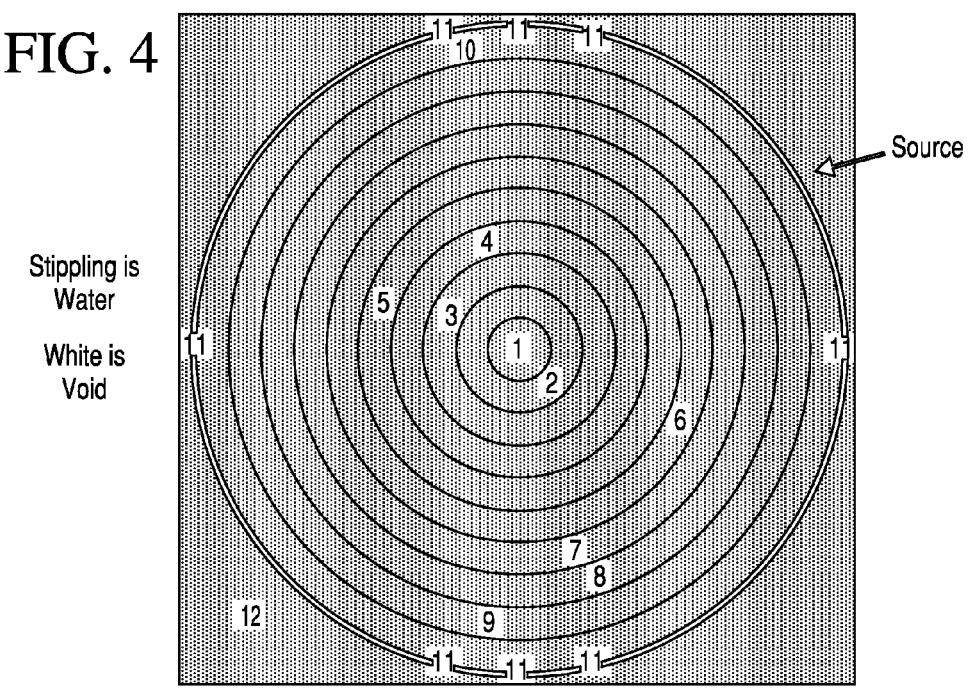
Figure 5:
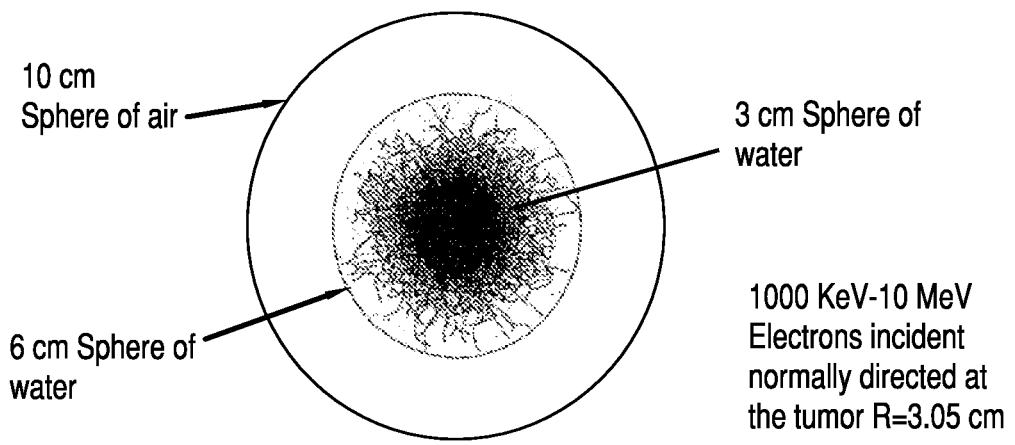
Figure 6:
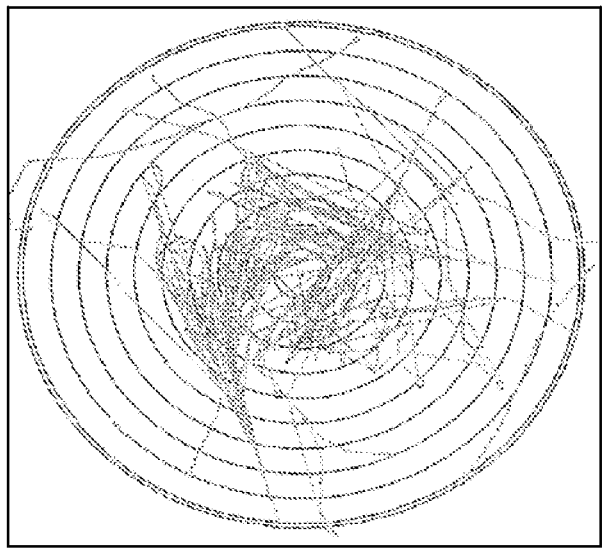

In another embodiment, the brachytherapy device 110 can include a compact, miniature laser driven dielectric accelerator 112' as the brachytherapy particle source (shown in FIG. 2B). The laser driven dielectric accelerator 112' includes dielectric structures 210 enclosing a vacuum channel 200. The dielectric structures 210 can include, but are not limited to, planar waveguide structures, periodic phase reset structures, hollow core PBG fibers, or 3-D photonic bandgap structures. High voltage gradients can be generated in the vacuum channel 200 using a laser beam, so that the particles entering the channel from an integrated particle generator 250 are accelerated as they travel through channel 200, as described, for example, in "Laser-Driven Dielectric-Structure Accelerators" by Eric R. Colby, "Light sources based on optical-scale accelerators" by Gil Travish, and "The Micro Accelerator Platform: A Potential Injector for a DLA Based Collider" by Gil Travish, all incorporated herein by reference in their entireties.

The particle generator 250 injects into the accelerator channel 200 particles, such as electrons, for example, which then are accelerated in the accelerator channel 200 while moving therethrough. The accelerator channel 200 can include a plurality of cavities/sections 220, 230, 240 configured to condition the entering electrons to form electron packets before leaving the accelerator 112' and to accelerate the electrons from a few keV to 1-10 MeV. The electrons conditioned in this manner arrive at a secondary source (not shown), such as a solid target, or to the delivery/treatment zone 102 at the same time and with energies in the range of 1-10 MeV, which can then be used directly to treat the patient. Electron packets are obtained by bunching the flow of electrons from the particle generator 250 and by slowing down the early electrons and accelerating the later electrons and doing nothing to the electrons which arrive at the "right time". The bunching is done in the first cavity/section 220 which is a particle buncher/chopper cavity 220. The second cavity 230 is a pre-accelerator cavity used to enhance the electron bunching and to accelerate the electrons. In this pre-acceleration stage, the increase in the electron beam energy matches the changing cavity low Beta structure, Beta being the ratio of electron velocity to velocity of light. In cavity/section 240, which is a high energy accelerator cavity, the electrons are accelerated to increase the electron beam energy from a few keV up to 1-10 MeV.

The particle generator 250 can include, but is not limited to, a pulsed RF gun, a Field Emitter Cathode, a laser photocathode RF gun, a diode or gridded gun, or a modulated anode generating a high voltage (HV) in the range of 5-20 kV, or any other applicable particle generators. In an embodiment, the particle generator can be an integrated laser photocathode RF gun as disclosed in "Generation of Femtosecond Electron Single Pulse using laser Photocathode RF Gun" by M. Uesaka et al. and incorporated herein by reference in its entirety or a photoinjector gun available from RadiaBeam Technologies. The particle source 250 is driven by a laser light from laser source 260, which can also supply the high energy voltage (HV) necessary for the generation of the high voltage gradients in the accelerator 112'. The laser driven dielectric accelerator 112' can have a diameter between 1-4 mm and a length between 2-4 mm and the dielectric structures 210 may be made of silica or any other suitable applicable materials.

The electronic brachytherapy system 100 can further include one or more radiation dosimeters (radiation sensors) 160 to detect and verify the actual dose delivered to one or more locations near the tissue to be irradiated. Some of the dosimeters 160 may be located directly on the applicator 111, some may be inserted into the body 120 at or near the condition to be treated, and some may be positioned on a second catheter at a location near the irradiated tissue. Because particle brachytherapy sources have a range, the dosimeters 160 are positioned within the treatment range in order to register any significant amount of dose. This is different from the conventional photon-based electronic brachytherapy systems, where dosimeters can be outside of the treatment range, or even outside the patient, and still be useful for modeling the dose delivered to the target tissue.

The one or more dosimeters 160 may be in wired or wireless communication with a computer processing system 150 including a processing device 151 and a controlling device 152. The dosimeters 160 provide feedback as to the dose received at the target tissue itself (tissue to be treated), as well as the dose that tissues other than the target tissue receive. This dose measurement provides critical information/data about whether the correct dose is administered to the target and whether other tissues and organs are also being irradiated with unacceptable levels of doses. This information can be relayed in real or near real time to the processing system 150 and may be used to change a predetermined treatment plan in real time or near real time (within a fraction of the real time). Because a full treatment dose of 50-100 Gy could be delivered to the patient within a few minutes, real-time dose monitoring is an important feature. If a pulse it too high or low one will need to know this in real time in order to adjust or stop the treatment. Additionally, the placement of the dosimeters 160 as well as the anticipated/predicted dose fields can be verified prior to full scale treatment. Also generating a record of the treatment can assist if there are complications that arise at a later time.

The treatment plan may include a previously determined treatment plan or may be a treatment plan inputted by a user, and may include a software program stored in a computer readable medium, such as but not limited to a disk, CD, hard drive, etc., to be executed by the processing device. The treatment plan can include (contain) variables that can be changed based on a set of information, data, readings, etc. received from one or more of the dosimeters 160. The controller 152 may also be in communication with the brachytherapy applicator 111, the brachytherapy source 112 through connection 153, as well as the laser source 130, and the gas source 140. The controller 152 is configured to modify the laser source 130 variables, such as the laser frequency, laser power output, laser energy output, and laser pulse width etc., the gas source 140 variables, such as, the amount of gas, and the turning the gas on and off, etc., as well as the mechanical variables associated with the brachytherapy applicator 111 and the brachytherapy source 112, such as the positioning of the source 112 within the applicator 111 and the positioning of the applicator 111 within the patient, etc., based on the actual radiation measured by the dosimeters 160. The treatment plan may also include variables relating to the placement of the dosimeters 160 as well as the anticipated/predicted dose fields.

In operation, after the region of irradiation (target region) is delineated and the type of particle treatment has been selected (although the type of particle could be a variable), a computer processing system 150 executes a treatment plan to deliver a predetermined dose to the target tissue. The treatment plan can be continuously adjusted for optimal dose delivery based on the real-time data received from the dosimeters 160. Factors, such as, but not limited to, particle type, particle energy (constrained to less than or equal to the upper limit for the selected particle type), particle fluence (i.e., the number of particles/unit area), particle directionality (i.e., direction of the particles), the solid angle of the tumor treated, time in each location, and the number of locations to treat (constrained to be less than some upper limit) can be continually adjusted (optimized) based on the received dosimetry data in order to deliver the prescribed dose.

The dosimeters 160 can include any applicable dosimeters, such as, but not limited to, MOSFET (metal—oxide—semiconductor field-effect transistor) in vivo dosimeters, real-time in vivo optical fiber dosimeters, scintillating fibers coupled to photodiodes, silicon detectors, or other solid state detectors packaged in such a way as to be able to be used as a real-time dose monitoring equipment.

The laser accelerator driven particle electronic brachytherapy device 110 can be used in treating lung cancers. Tumors in the lung are especially problematic to treat with radiation because of the movement of the tumor during breathing, the delicate nature of lung structure, the buried (protected) nature of the lungs beneath the rib cage, and many other critical structures that are directly in line with the radiation beams. Using Intensity Modulated Radiation Therapy (IMRT) or Image Guided Radiation Therapy (IGRT) is presently the treatment method used for external beam therapy, but accurate real time tracking the location of the tumor is a problem. Promising results are arising from Carbon ion or Proton treatments. Currently, however, there are limited methods to track tumors in 4D. With treatment times of 10 minutes or more, using 4D CT (4D Computed Tomography) to track tumors delivers an unacceptably high dose to the target tissue. Magnetic Resonance Imaging (MRI) can track lung tumors in real time. The available electronic brachytherapy (EBT) systems can also be used. Based on recent studies regarding the effect of magnetic fields on the dose distribution of particle beams, the particle based electronic brachytherapy device 110 with an MRI style magnet could be used in treating lung tumors because the penumbra of electron beams can be controlled and in some instances eliminated by the application of magnetic fields. Therefore, the dose can be deposited more advantageously and healthy regions (tissues, organs, etc.) may be spared.

Surrogates can also be used to measure the movement of the chest and algorithms can be used to correlate the tumor position to the surrogate. This works fairly well but tends to drift over the course of several minutes requiring the acquisition of new CT scans. As beam delivery continues to improve, the accuracy of the radiation delivery exceeds the accuracy measuring the tumor position. This uncertainty causes more radiation to be delivered than necessary and to a larger volume than desired. Therefore, delivery of a particle based electronic brachytherapy source 112 via a bronchoscope directly into the lung and adjacent to the tumor allows precise delivery of radiation to the tumor and very little radiation to the surrounding healthy tissue (due to the Bragg peak for protons or other ion), or finite range of the emitted particles. The distance that a particle travels into the tissue is directly related to its energy. Guiding a bronchoscope to the suspected tumor can be accomplished as is described in U.S. Pat. No. 7,233,820 and U.S. Pat. No. 7,555,330 and incorporate herein by reference in its entirety. Dosimeters 160 on the treatment catheter 111 or delivered by a second catheter or otherwise inserted into the body 120 may be used to verify the dose delivered, and/or can be used to change the treatment plan in real time or near real time within the fraction.

The currently available treatment planning software cannot model particle-based therapies and therefore, new treatment planning system software is also needed. The Treatment Planning System (TPS) software models the electron or proton therapy when the brachytherapy source 112 is inside the body 120. The TPS can include treatment prescription, particle type and dwell positions as inputs, and particle energy, and dwell time as outputs. The catheter 111 may move with the portion of the lung containing the tumor, keeping the tumor and treatment source 112 aligned at all times, thus eliminating the need for imaging the tumor. The treatment planning software (process) can be stored in a non-transitory computer readable medium, such as disks, CD-ROMs, etc. and executed using a computer processing system 150 including any software and hardware modules necessary for execution of the process in a particular application. A sequence of programmed instructions is embodied upon the computer-readable storage medium for treating a condition within the body of a patient based on particle-based brachytherapy so that when a computer processing system executes the sequence of programmed instructions embodied on the computer-readable storage medium it causes the computer processing system to perform the steps of: inputting treatment prescription, particle type and particle beam dwell positions, outputting particle energy, and particle beam dwell time, and automatically generating a new and/or modifying a predetermined treatment plan based on the outputted information. The new and/or modified treatment plan may allow the particle-based electronic brachytherapy applicator 111 to move with the portion of the organ containing the tumor, keeping the tumor and treatment source aligned at all times.

In operation, after the region of irradiation is delineated and the type of particle treatment has been selected (although the type of particle could be a variable), a computer processing system 150 executes a treatment plan to deliver a predetermined dose to the target tissue. The treatment plan can be continuously adjusted for optimal dose delivery based on the real-time data received from the dosimeters 160. Factors, such as, but not limited to, particle type, particle energy (constrained to less than or equal to the upper limit for the selected particle type), particle fluence (i.e., the number of particles/unit area), particle directionality (i.e., direction of the particles), the solid angle of the tumor treated, time in each location, and the number of locations to treat (constrained to be less than some upper limit) can be continually adjusted (optimized) based on the received dosimetry data in order to deliver the prescribed dose.

In another variation, a robot similar to the one developed by Intuitive Surgical and the Da Vinci robot can be used to place the particle-based electronic brachytherapy source 112 as well as the dosimeters 160 with high precision and repeatability. Because the particle brachytherapy source 112 has a range, the dosimeters 160 are positioned within the treatment range or they will not register any significant amount of dose.

The particle based brachytherapy device 110 can also be used to treat an eye condition with protons. Radiation treatment of the macula of the eye has been shown to be an effective treatment for Wet AMD (Age related Macular Degeneration). Various methods have been proposed for delivering the radiation to the macula without damaging other structures of the eye. Delivery of radiation from a micro miniature X-ray source of an electronic brachytherapy device to the eye is done behind the eye through a cut in the conjunctive and placed opposed the macula through the intervening sclera. A system and method for using a photon-based electronic brachytherapy device to treat an eye condition is described in U.S. Pat. No. 7,351,193. Systems where the radiation is delivered to the macula via a large X-ray source from the front of the eye using three or more ports or delivery angles are also described in U.S. Pat. No. 7,564,946, U.S. Pat. No. 7,620,147, U.S. Pat. No. 7,680,244, U.S. Pat. No. 7,680,245 and U.S. Pat. No. 7,693,258. Such delivery systems and methods are designed to reduce the dose to the sclera while delivering a therapeutic dose to the macula. All of these treatments, however, have disadvantages. Delivering radiation sources behind the eye is invasive and requires careful placement of the source directly behind the macula. Delivering radiation external to the eye with high energy X-rays also delivers radiation dose to the brain directly behind the eye. The particle-based brachytherapy device 110 with accelerated protons as the beam source can provide a non-invasive treatment therapy for any eye condition. This can be made possible because protons and heavy ions have the distinct advantage that they deposit the majority of their energy at the end of the range (Bragg Peak) along the propagation axis, and therefore allow for an improved uniform dose distribution.

Figures 7, 8:
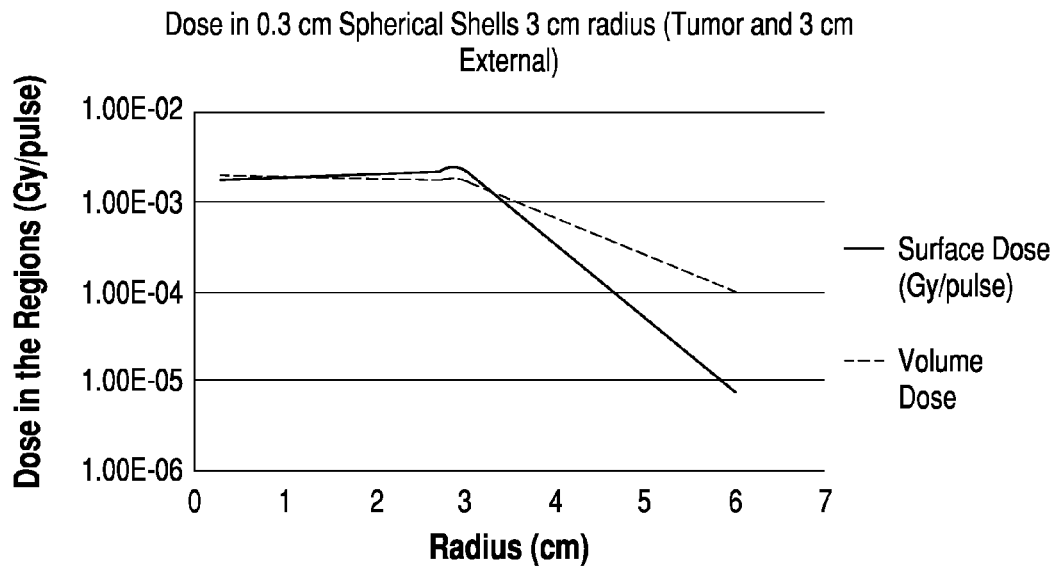
FIG. 7 is a graph showing a dose distribution for 10 MeV electrons incident on a 3 cm radius of water sphere, in accordance with an embodiment of the invention.
FIG. 8 is a tabular illustration of data obtained from a simulation for 10 MeV electrons incident on a 3 cm water sphere, in accordance with various embodiments of the invention.

Simulation results for 10 MeV electrons incident on a 3 cm sphere of water are shown in FIGS. 3-6. FIG. 7 is a graph showing a dose distribution for 10 MeV electrons incident on a 3 cm radius of water sphere, and FIG. 8 is a tabular illustration of data obtained from a simulation for 10 MeV electrons incident on a 3 cm water sphere.

It is therefore, apparent that there is provided, in accordance with the present disclosure, a system, apparatus and method for particle-based electronic brachytherapy device for applying particle beam radiation to a target structure within a body part comprising an applicator for insertion toward a desired location within the body part for effecting particle beam radiation therapy, and a particle source positioned within the applicator for generating particle beams having energies between 5-70 MeV. The particle source can be a laser driven accelerator such as, but not limited to, a laser plasma accelerator or a laser driven dielectric accelerator. It is also apparent that there is provided, in accordance with the present disclosure, a system for applying particle beam radiation to a target structure, comprising a laser powered accelerator driven device for emitting particle beam radiation to a target structure upon commencement of a radiation therapy, the device including an applicator for insertion toward a desired location within the body part, and a laser driven accelerator positioned within the applicator for generating the particle beams, a laser source for generating a laser beam, a laser delivery device for delivering the laser beam from the laser source to the laser driven accelerator, one or more radiation sensors positioned adjacent the target structure and within a treatment range for real-time particle radiation dose measurement, and a processing system in communication with the laser source, the device, and the radiation sensors, for continuously adjusting particle radiation beam parameters based on the radiation dose measured by the radiation sensors. A brachytherapy catheter is also provided comprising a catheter body member and a miniature particle source positioned within the catheter body member to generate particle beams having energies between 5-70 MeV.

A method for treating a patient with particle radiation therapy, comprising inserting an applicator to a desired location within the patient, the applicator including a source for generating particle beam radiation having an energy between 5-70 MeV, and delivering particle beam radiation to a treatment region is also disclosed. Additionally, a treatment plan stored in a non-transitory computer readable medium for treating a condition within a body part of a patient based on laser powered accelerator driven particle based brachytherapy is also disclosed wherein instructions are executed by a computer processing system to perform the steps of: generating a treatment plan based on treatment prescription, particle type, and particle dwell time, delivering particle radiation treatment based on the treatment plan, acquiring particle radiation information from one or more radiation sensors, determining particle energy and particle dwell time based on the acquired information, and adjusting the treatment plan based on the outputted information.

Many alternatives, modifications, and variations are enabled by the present disclosure. Features of the disclosed embodiments can be combined, rearranged, omitted, etc. within the scope of the invention to produce additional embodiments.

Furthermore, certain features of the disclosed embodiments may sometimes be used to advantage without a corresponding use of other features. Accordingly, Applicants intend to embrace all such alternatives, modifications, equivalents, and variations that are within the spirit and scope of the present disclosure.

While embodiments and applications of this invention have been shown and described, it would be apparent to those skilled in the art that many more modifications are possible without departing from the inventive concepts herein. The invention is not limited to the description of the embodiments contained herein, but rather is defined by the claims appended hereto and their equivalents.

What is claimed is:

1. A brachytherapy device for applying particle beam radiation to a target region within a patient, comprising:
   an applicator configurable as a catheter for insertion toward a desired location within the patient for effecting particle beam radiation therapy; and
   a laser driven accelerator positioned within the applicator for generating particle beams having energies between 5-70 MeV,
   the laser driven accelerator comprising an accelerator cavity including a particle generating medium and a particle accelerating medium, an input end portion allowing laser light to enter the accelerator cavity and drive particle generation and particle acceleration, and an output aperture through which accelerated particles exit the laser driven accelerator as particle beams.

2. The brachytherapy device of claim 1, wherein the particle beams include electrons, protons, or heavy ions.

3. The brachytherapy device of claim 1, wherein the laser driven accelerator is one of a laser plasma accelerator and a laser dielectric accelerator.

4. The brachytherapy device of claim 3, wherein the laser driven accelerator is a laser plasma accelerator, which includes:
   a target within the accelerator cavity, the target comprising matter which forms a plasma upon exposure to one or more laser light pulses or to an electrical discharge; and
   an optical device positioned in the cavity to direct incoming laser light into the plasma for generating a plasma wave and for injecting particles into the plasma for acceleration using the plasma wave.

5. The brachytherapy device of claim 4, wherein the target is a gas.

6. The brachytherapy device of claim 5, further comprising:
   a gas delivery member for delivering gas into the accelerator cavity from an external gas source.

7. The brachytherapy device of claim 6, wherein the gas includes hydrogen or helium.

8. The brachytherapy device of claim 4, wherein the optical device includes one or more mirrors.

9. The brachytherapy device of claim 4, wherein the laser plasma accelerator includes high voltage electrodes for generating the electrical discharge.

10. The brachytherapy device of claim 4, wherein the laser plasma accelerator further includes a guiding member disposed along a length of the applicator for directing laser light toward a laser dumping device after particle acceleration.

11. The brachytherapy device of claim 4, further comprising:
    a laser delivery member for delivering the laser light from an external laser source into the accelerator cavity.

12. The brachytherapy device of claim 4, wherein the laser plasma accelerator has a diameter between 50-400 micrometers and a length between 1-2 mm.

13. The brachytherapy device of claim 3, wherein the laser plasma accelerator is made of a flexible material.

14. The brachytherapy device of claim 1, wherein the applicator is made of a flexible material.

15. The brachytherapy device of claim 1, wherein the applicator has a length of about 2-10 mm and a diameter of about 0.5-6 mm.

16. The brachytherapy device of claim 1, further comprising a secondary radiation source positioned in the applicator to generate secondary radiation beams.

17. The brachytherapy device of claim 16, wherein the secondary radiation source includes a second target positioned adjacent the laser driven accelerator such that the particles generated in the laser driven accelerator, upon exiting the laser driven accelerator, strike the second target, thereby generating X-rays, gamma rays, or neutrons.

18. The brachytherapy device of claim 16, wherein the secondary radiation source includes a second target positioned adjacent the laser driven accelerator such that the particles generated in the laser driven accelerator, upon exiting the laser driven accelerator, strike the second target, thereby generating X-rays, gamma rays, and neutrons.

19. The brachytherapy device of claim 1, further comprising a radiation dose detecting device detachably attached to an outside surface of the applicator for detecting a particle radiation dose delivered to the target region.

20. The brachytherapy device of claim 1, wherein the particle beams include electrons, protons, and heavy ions.

21. A system for applying particle beam radiation to a target region of a patient, comprising:
    a laser driven device for emitting particle beam radiation to the target region upon commencement of a radiation therapy, the laser driven device including an applicator for insertion toward a desired location within the patient, and a laser driven accelerator positioned within the applicator for generating particle beams, the laser driven accelerator comprising an accelerator cavity including a particle generating medium and a particle accelerating medium, an input end portion allowing a laser beam to enter the accelerator cavity and drive particle generation and particle acceleration, and an output aperture through which accelerated particles exit the laser driven accelerator as particle beams;
    a laser source for generating the laser beam;
    a laser delivery device for delivering the laser beam from the laser source to the laser driven accelerator;
    one or more radiation sensors positioned adjacent the target region and within a treatment range for real-time particle radiation dose measurement; and a processing system in communication with the laser source, the laser driven device, and the radiation sensors, for adjusting particle radiation beam parameters based on the radiation dose measured by the radiation sensors.

22. The system of claim 21, wherein the particle beams include electrons, protons, or heavy ions.

23. The system of claim 21, wherein the particle beams have energies between 5-70 MeV.

24. The system of claim 21, wherein the laser driven accelerator includes one of a laser plasma accelerator and a laser dielectric accelerator.

25. The system of claim 24, wherein the device further includes a gas source and a gas delivery device for delivering plasma gas into the laser plasma accelerator.

26. The system of claim 25, wherein the processing system is further configured to adjust the gas source variables.

27. The system of claim 26, wherein the gas source variables include amount of gas and gas source on/off status.

28. The system of claim 24, wherein the laser driven accelerator is a laser plasma accelerator, which includes:
a target within the accelerator cavity, the target comprising matter which forms a plasma upon exposure to one or more laser light pulses or to an electrical discharge; and
an optical device positioned in the cavity to direct incoming laser light into the plasma for generating a plasma wave and for injecting particles into the plasma for acceleration using the plasma wave.

29. The system of claim 21, wherein the particle radiation beam parameters include particle type, particle energy, particle fluence, particle directionality, solid angle of the target region, radiation exposure time, and number of different radiation treatment locations within the target region.

30. The system of claim 21, wherein the processing system is further configured to adjust laser source variables and mechanical variables.

31. The system of claim 30, wherein the laser source variables include laser frequency, laser power output, laser energy output, and laser pulse width.

32. The system of claim 30, wherein the mechanical variables include position of the laser driven accelerator within the applicator and the position of the applicator within the patient.

33. The system of claim 21, wherein the processing system is further configured to execute a predetermined treatment plan for delivering a predetermined radiation dose to the target region and to adjust in real-time the treatment plan based on the radiation dose measured by the radiation sensors.

34. The system of claim 31, wherein the one or more radiation sensors are in a wireless communication with the processing system.

35. The system of claim 21, wherein the laser source includes a chirped laser amplification system (CPA).

36. The system of claim 21, wherein the device is an electronic brachytherapy device.

37. The system of claim 21, wherein the particle beams include electrons, protons, and heavy ions.

38. A brachytherapy catheter, comprising:
a catheter body member; and
a miniature laser driven accelerator positioned within the catheter body member to generate particle beams having energies between 5-70 MeV,
the laser driven accelerator comprising an accelerator cavity including a particle generating medium and a particle accelerating medium, an input end portion allowing laser light to enter the accelerator cavity and drive particle generation and particle acceleration, and an output aperture through which accelerated particles exit the laser driven accelerator as particle beams.

39. The brachytherapy catheter of claim 38, wherein the particle beams include electrons, protons, and/or heavy ions.

40. The brachytherapy catheter of claim 38, wherein the miniature laser driven accelerator includes a laser plasma accelerator including:
a target within the accelerator cavity, the target comprising matter which forms a plasma upon exposure to one or more laser light pulses or to an electrical discharge; and
an optical device positioned in the cavity to direct incoming laser light into the plasma for generating a plasma wave and for injecting particles into the plasma for acceleration using the plasma wave.

41. The brachytherapy catheter of claim 38, wherein the miniature laser driven accelerator includes a laser driven dielectric accelerator.

42. A method of treating a patient directly with particle radiation therapy, comprising:
inserting an applicator to a desired location within the patient, the applicator including a laser driven accelerator for generating particle beam radiation having energies between 5-70 MeV, the laser driven accelerator comprising an accelerator cavity including a particle generating medium and a particle accelerating medium, an input end portion allowing laser light to enter the accelerator cavity and drive particle generation and particle acceleration, and an output aperture through which accelerated particles exit the laser driven accelerator as particle beams; and
delivering the particle beam radiation to a treatment region.

43. The method of claim 42, wherein the laser driven accelerator includes a laser plasma accelerator.

44. The method of claim 43, wherein the generating includes:
generating plasma inside the laser plasma accelerator;
delivering a first laser pulse into the laser plasma accelerator to generate a laser plasma wave;
injecting particles into the laser plasma using a second laser pulse to accelerate the particles using the laser plasma wave.

45. The method of claim 42, wherein the laser driven accelerator includes a laser driven dielectric accelerator.

46. The method of claim 42, wherein the particles include electrons, protons, or heavy ions.

47. The method of claim 42, wherein the delivering includes delivering the particle beam radiation based on a treatment plan.

48. The method of claim 47, further comprising adjusting in real-time the treatment plan based on information received from one or more radiation sensors positioned within a radiation target range.

49. The method of claim 47, wherein the treatment plan includes one or more variables that are adjustable based on the received radiation sensor information.

50. The method of claim 47, wherein the variables include particle type, particle energy, particle fluence, particle directionality, solid angle of the treatment region, radiation exposure time, and number of different radiation treatment locations within the treatment region.

51. The method of claim 47, further including adjusting the variables by adjusting one or more of laser source variables, gas source variables, and mechanical variables.

52. The method of claim 42, wherein the particles include electrons, protons, and heavy ions.

53. A sequence of programmed instructions stored in a non-transitory computer readable medium for treating a condition within a patient based on laser accelerator driven particle electronic brachytherapy using a brachytherapy device including an applicator and a laser driven accelerator positioned therewithin, the laser driven accelerator comprising an accelerator cavity including a particle generating medium and a particle accelerating medium, an input end portion allowing laser light to enter the accelerator cavity and drive particle generation and particle acceleration, and an output aperture through which accelerated particles exit the laser driven accelerator as particle beams, the instructions being executed by a computer processing system, comprising:

generating a treatment plan based on treatment prescription, particle type, and particle dwell time;
delivering particle radiation treatment based on the treatment plan;
acquiring in real time particle radiation information from one or more radiation sensors;
determining particle energy and particle dwell time based on the acquired information;
outputting determined particle information; and
adjusting in real time the treatment plan based on the outputted information.

\* \* \* \* \*